US008722345B2

(12) United States Patent
Zhang

(10) Patent No.: US 8,722,345 B2
(45) Date of Patent: *May 13, 2014

(54) METHODS FOR MEASURING PROTEIN CONTENT

(71) Applicant: Jiandi Zhang, Fairfax, VA (US)

(72) Inventor: Jiandi Zhang, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/732,434

(22) Filed: Jan. 1, 2013

(65) Prior Publication Data

US 2013/0177930 A1 Jul. 11, 2013

Related U.S. Application Data

(63) Continuation-in-part of application No. 13/656,715, filed on Oct. 21, 2012, now Pat. No. 8,563,256, which is a continuation of application No. 13/459,192, filed on Apr. 29, 2012, now Pat. No. 8,293,487.

(60) Provisional application No. 61/583,624, filed on Jan. 6, 2012.

(51) Int. Cl.
*G01N 33/53* (2006.01)

(52) U.S. Cl.
USPC ............................................ 435/7.1; 435/7.2

(58) Field of Classification Search
None
See application file for complete search history.

(56) References Cited

U.S. PATENT DOCUMENTS 8,293,487 B1   10/2012   Zhang

OTHER PUBLICATIONS

Burnette, W. N. "Western blotting": Electrophoretic transfer of proteins from sodium dodecyl sulfate-polyacrylamide gels to unmodified nitrocellulose and radiographic detection with antibody and radioiodinated protein A. Analytical Biochemistry (1981) V. 112, pp. 195-203.
Hawkes, R., Niday, E., Gordon, J. A dot-immunobinding assay for monoclonal and other antibodies. Analytical Biochemistry (1982) V.119, pp. 142-147.
Engvall, E., Jonsson, K., Perlmann, P.. Enzyme-linked immunosorbent assay II. Quantitative assay of protein antigen, immunoglobulin G, by means of enzyme-labeled antigen and antibody-coated tubes. Biochemica et biophysica acta (1971) V. 251, pp. 427-434.

Engvall, E., Perlmann, P.. Enzyme-linked immunosorbent assay, ELISA III. Quantitation of specific antibodies by enzyme-labeled anti-immunoglobulin in antigen-coated tubes. The Journal of Immunology (1972) V. 109, pp. 129-135.
Yalow, R.S., Berson, S.A.. Immunoassay of endogenous plasma insulin in man. Journal of Clinical Investigation (1960) V. 39, pp. 1157-1175.
Zhang, J.. The direct involvement of SirT1 in insulin-induced insulin receptor substrate-2 tyrosine phosphorylation (2007). V. 282, pp. 34356-34364.
Sekar, R. B., Periasamy, A.. Fluorescence resonance energy transfer (FRET) microscopy imaging of live cell protein localizations (2003). V. 160, pp. 629-633.
Burnette, W. N. "Western blotting": Electrophoretic transfer of proteins from sodium dodecyl sulfate-polyacrylamide gels to unmodified nitrocellulose and radiographic detection with antibody and radioiodinated protein A. Analytical Biochemistry (1981) V.112, pp. 195-203.
Hawkes,R., Niday, E., Gordon,J.A. A dot-immunobinding assay for monoclonal and other antibodies. Analytical Biochemistry (1982) V.119, pp. 142-147.
Engvall, E., Perlmann, P.. Enzyme-linked immunosorbent assay (ELISA). Quantitative assay of immunoglobulin G. Immunochemistry (1974) V. 8, pp. 871-874.
Engvall, E. Jonsson, K., Perimann, P..Enzyme-linked immunosorbent assay II. Quantitative assay of protein antigen, immunoglobulin G. by means of enzyme-labeled antigen and antibody-coated tubes. Biochemica at biophysica acta (1971) V. 251, pp. 427-434.
Engvall, E. Perlmann, P.. Enzyme-linked immunosorbent assay, ELISA III. Quantitation of specific antibodies by enzyme-labeled anti-immunoglobulin in antigen-coated tubes. The Journal of Immunology (1972) V. 109, pp. 129-135.
Yalow, R. S., Berson, S. A.. Immunoassay of endogenous plasma insulin in man. Journal of Clinical Investigation (1960) V. 39, pp. 1157-1175.
Zhang, J. The direct involvement of SirT1 in insulin-induced insulin recepor substrate-2 tryosine phosphorylation (2007) V. 282, pp. 34356-34364.
Sekar, R. B. Periasamy, A.. Fluorescence resonance energy transfer (FRET) microscopy imaging of live cell protein localizations (2003) V. 160, pp. 629-633.
Bosse, R., Illy, C., Chelsky, D.. Application note: Principles of AlphaScreen. Amplified Luminescent proximity Homogenous assay (2002). PerkinElmer Life Sciences. AlphaScreen application note ASC-001.

*Primary Examiner* — Jacob Cheu

(57) ABSTRACT

A process for measuring the amount of an antigen in a sample comprising the steps of binding the antigen to a solid phase, forming an antigen-antibody immunocomplex on the solid phase by applying a detection antibody that is specific for the antigen, liberating the detection antibody from the immunocomplex by applying a competing molecule that disrupts the immunocomplex by competing against the antigen for binding to the detection antibody, collecting the liberated detection antibody; and quantifying the liberated detection antibody to measure the amount of the antigen in the sample.

28 Claims, 2 Drawing Sheets

METHODS FOR MEASURING PROTEIN CONTENT

RELATED APPLICATIONS

This application is a Continuation-in-part of U.S. patent application Ser. No. 13/656,715 filed Oct. 21, 2012, which is a continuation of U.S. patent application 13/459,192 filed Apr. 29, 2012, now U.S. Pat. No. 8,293,487, which claims priority to U.S. Provisional Patent Application No. 61/583,624 filed Jan. 6, 2012. Each of these applications is incorporated in its entirety into this application.

FIELD OF THE INVENTION

The present invention relates to an immunodetection process for an antigen such as a chemical compound, a peptide, a protein, an RNA, a DNA, a cell (proteins released in situ), or a virus particle (proteins released in situ). In particular, this invention provides simple and improved method with quantifiable result for performing immunodetection assays including but not limited to Western blot analysis, Dot analysis, ELISA assay and their applications in multi-unit plate format, and automation of protein analysis.

BACKGROUND

Protein analysis is the fundamental basis of modern biology research. It centers on antigen-antibody interaction to measure levels of antigen of interest under various medical or experimental conditions. An antigen by definition, is a foreign molecule that, when introduced into the body, triggers the production of an antibody by the immune system. The high specificity of the antibody against a specific antigen makes it a powerful tool in clinical, pharmaceutical and biomedical research. An antigen includes, but not limited to a chemical compound, a peptide, a protein, an RNA, a DNA, a cell (proteins released in situ), or a virus particle (proteins released in situ). The whole molecule of antigen, or part of the molecule, may be introduced into a host animal, such as a donkey, a goat, or a rabbit to generate large quantity of antibody against the introduced antigen of interest. Furthermore, the introduced antigen, or part of the antigen, may have one or several epitopes, thus may generate one or several antibodies against the antigen of interest depending on the number of epitope(s) available.

A typical immunodetection process can be divided into three major steps, including, (i), Sample application, where prepared samples containing an antigen of interest are first bound to a membrane, such as nitrocellulose or PVDF membrane or other solid phase like multi-well plate with protein binding capacity; (ii), blocking/incubation/washing step, which includes multiple sub-steps, where first (a), non-specific protein binding sites on the membrane are blocked using blocking buffer to avoid non-specific protein binding to the membrane; next (b), the membrane is incubated with antibody against antigen of interest to allow for the formation of membrane-bound antigen-antibody complex while unbound antibodies are washed away. In this sub-step, the antibody used may be directly labeled, or indirectly labeled through a secondary antibody, with a reporter enzyme; and (iii), detection, enzymatic reaction is initiated using reporter enzyme coupled with membrane-bound antibody in a reporter assay to give a readout comprising information related to the quantity or quality of the bound immunocomplex on the membrane. In both Dot blot analysis and Western blot analysis, the final result of the immunodetection analysis can be further quantified indirectly through densitometric analysis.

Multiple modifications have been made to this generalized procedure in each individual step. For example, in step (i), there are variations of sample application, including direct application in Dot blot analysis, gel transfer in Western blot analysis and coating of samples in ELISA analysis. Several more modifications have been made in step (ii), including the various procedures and buffer compositions to maximally eliminate direct antibody binding while preserving the formed immunocomplex on the membrane. In most cases, the primary antibody is not directly labeled with reporter enzyme. A reporter enzyme coupled-secondary antibody against the primary antibody maybe needed to label those primary antibodies bound to the antigen of interest on the surface of membrane. In step (iii), besides reporter enzyme, a number of different methods have been used to label the antibody, which, in turn, may lead to various detection methods. For example, the readout may result in color for visual inspection or a chemiluminescence signal that can be detected either through luminometer or X-ray film. The antibody may also be fluorescence-labeled, and the final product is quantified at different wavelength in a microplate reader.

While this generalized description of the immunodetection process is merely illustration of the principles underlying the conventional immunodetection analysis, it is by no means to exhaust all the methods or modifications associated with this process. There are always modifications or procedures not described here, yet consistent with the scope and the spirit of this generalized immunodetection process.

Dot blot analysis is a typical application of the above described immunodetection process, symbolized by the direct application of the prepared samples on to membrane in a dot. However, although this process is simple and fast, its application in biomedical, clinical and pharmaceutical research is limited by its lack of specificity. In multiple cases, antibody used in immunodetection assay reacts with more than one antigen for various reasons. Therefore, the amount of the reporter enzyme associated with bound immunocomplex in a Dot blot analysis cannot reflect reliably the amount of the antigen of interest in prepared samples. Consequently, both Western blot analysis and ELISA assay are more commonly used due to improved specificity.

In Western blot analysis, prepared samples containing the antigen of interest are first separated by their molecular weight though gel electrophoresis, and the separated proteins are transferred through electroblotting step to either nitrocellulose membrane or PVDF membrane. Followed by a typical immunodetection process, the levels of the antigen of interest in the prepared samples are detected on the spot in a typical reporter enzyme-based reaction, and quantified indirectly through densitometric analysis. In this process, the specificity of immunodetection is achieved by both the antigen-antibody interaction as well as the expected molecular weight of the antigen of interest to eliminate any false signals commonly observed in Dot blot analysis. However, in both Dot blot analysis and Western blot analysis, the relative amount of the antigen of interest can only be quantified indirectly through densitometric analysis. Also, in Western blot analysis, the complicated procedures may prevent its application in large-scale analysis in clinical, pharmaceutical and experimental research.

On the other hand, ELISA assay successfully avoids problems associated with both Dot blot analysis and Western blot analysis to allow fast, simple and quantifiable results in a multi-well plate format. The specificity of the assay is achieved by selecting antibody exclusively reacting with the antigen of interest. The high specificity of the antibody-antigen reaction also allows for direct quantification of signal intensity in multi-well plate format. These advantages lead to the wide usage of ELISA techniques in both biomedical and clinical research. Yet, the success of ELISA assay demands high specificity of the antibody, and only those reacting exclusively to the antigen of interest are acceptable for further development. This limitation leads to high developmental cost of successful ELISA assay and limits its availability in the field of biomedical research. In addition, the low binding capacity of the ELISA plate may also significantly limit its usage in the biomedical research field.

SUMMARY

The present disclosure provides methods that allow for rapid and accurate quantification of an antigen in a sample. The disclosed methods may eliminate the gel electrophoresis step in Western blot analysis while improving the specificity of the Dot blot assay by including an elution step in an immunodetection process. This additional step allows membrane-bound (i.e., immobilized) antigen-antibody immunocomplex to be exposed to excessive amount of a competing molecule, such as an antigen (or part of antigen) in single or multiple copies within a single molecule. In one aspect, the detection antibody may be labeled directly or indirectly with reporter enzyme. In another aspect, a competing molecule may be present in an elution solution. Competition between the competing molecule and the immobilized antigen to bind to the detection antibody may result in the liberation of the antibody from the bound immunocomplex into the elution solutions. The amount of report enzyme attached to the detection antibody liberated from the membrane may be quantified and the results may be used to calculate the amount of the antigen of interest in the sample. In one aspect, the amount of the antigen of interest in the sample is proportional to the amount of the detection antibody liberated from the solid phase. In another aspect, the antibody is not pre-labeled, and may be labeled after the elution step but before the quantification step.

In one embodiment, this added elution step may enhance the assay specificity, as only antibody bound to the antigen of interest can be displaced from the bound immunocomplex by the competing molecule. Compared with both Dot blot analysis and Western blot analysis, the disclosed method also allows direct quantification of the result of the immunodetection analysis in solution and in a multi-unit plate format, a feature highly desired in today's clinical and pharmaceutical studies and diagnostic applications. In addition, it also reduces the cost and efforts commonly associated with ELISA assay development to increase its availability in clinical, pharmaceutical and biomedical research and its diagnostic applications. Furthermore, it provides basis for protein array analysis and automation of the protein analysis process in clinical, biopharmaceutical and experimental research and their diagnostic applications. The disclosed method may also be used in an automated assay.

In one embodiment, the multi-unit plate is a multi-well plate.

In one embodiment, an improved immunodetection process based on Dot blot or Western blot analysis is disclosed to circumvent the limitations associated with currently available immunoassay techniques, with the distinct advantage of being simple, fast, directly quantifiable, specific, and suitable for large scale applications in clinical, pharmaceutical and experimental research and diagnostic applications.

In one embodiment, the disclosed process may include the following steps: binding the antigen to a solid phase; forming an antigen-antibody immunocomplex on the solid phase by applying a detection antibody that is specific for the antigen to the solid phase; liberating the detection antibody from the immunocomplex by applying a competing molecule that disrupts the immunocomplex by competing against the antigen for binding to the detection antibody; and quantifying the liberated detection antibody to obtain the amount of the antigen in the sample. The process may also include a step of collecting the liberated detection antibody after the eluting step. This process is named "Zestern" analysis.

In one aspect, the antigen may be immobilized to the solid phase by applying the sample or a portion the sample containing the antigen to the solid phase. In another aspect, after forming the immunocomplex but before liberating the detection antibody, antibody unbound to the immobilized antigen may be removed from the solid phase by a washing step.

In one embodiment, the competing molecule may be a polypeptide. In another embodiment, the competing molecule may be a polypeptide that contain an epitope of the antigen that is specific to the detection antibody. In another embodiment, the competing molecule may be a polypeptide that contain all epitopes of the antigen such that the competing molecule can effectively compete against the immobilized antigen for binding with the detection antibody. In another embodiment, the polypeptide may contain the antibody-interacting region of the antigen. In another embodiment, the antibody-interacting region of the antigen is present in multiple copies within the competing molecule. In another embodiment, the affinity between the polypeptide and the detection antibody is greater than that between the antigen and the detection antibody, thus allowing the polypeptide to effectively compete against the immobilized antigen for binding to the detection antibody. In another embodiment, the polypeptide is present in an amount (in molar) that is at least two times, three times, or more, as much as the amount (in molar) of the immobilized antigen. In one embodiment, the competing molecule can exist in a mixture of peptides.

In another embodiment, a process for measuring the amounts of multiple antigens in a sample is disclosed, which may include the following steps: taking multiple sub-samples from the sample; placing each sub-sample to a separate solid phase, perform the Zestern described above for each sub-sample. Alternatively, a different process may be employed for measuring the amounts of a plurality of antigens in a sample, which include the following steps: binding the plurality of antigens to a solid phase, forming a plurality of antigen-antibody immunocomplexes on the solid phase by applying a plurality of detection antibodies, each of which is specific for one of the plurality of antigens; liberating one of the detection antibodies from the solid phase by applying a competing molecule that disrupts the immunocomplex formed by that detection antibody and the corresponding antigen by competing against the antigen for binding to the detection antibody; collecting the liberated detection antibody; quantifying each liberated antibody to measure the amount of the corresponding antigen in the sample. The liberating step and the collective step may be repeated one or more times using different competing molecules that are specific for different detection antibodies.

In another embodiment, a process of measuring multiple antigens in a sample is disclosed, which may include the following steps: take multiple sub-samples from sample, applying each sub-sample to a separate solid phase, forming a plurality of test antigen-antibody immunocomplexes on the solid phase by applying a plurality of test detection antibodies, each of which is specific for one of the plurality of test antigens may or may not presence in the sample; liberating one of the test detection antibody from the one solid phase by applying a competing molecule that disrupts the immunocomplex formed by that test detection antibody and the corresponding test antigen. Performing this process with another solid phase with different competing molecule that disrupts the immunocomplex formed by another test detection antibody and the corresponding test antigen. Collecting the liberated detection antibodies and quantifying each liberated antibody to measure the amount of the corresponding test antigens in the sample.

The detection antibody may be labeled before the detection antibody is applied to the solid phase. Alternatively, the detection antibody may be unlabeled and is only labeled after elution before the measuring step. The detection antibody may be labeled directly or may be labeled indirectly via a secondary antibody. Methods of labeling the detection antibody may include but are not limited to radiolabeling, infrared labeling, fluorescence labeling or reporter-enzyme labeling.

In another embodiment, the detection antibody may be labeled with a first fluorescence label, and the competing molecule may be labeled with a second fluorescence label. The emitting wavelength and the excitation wavelength of the first and the second fluorescence labels may be selected so that fluorescence resonance energy transfer (FRET) may occur when the liberated detection antibody and the competing molecule form an immunocomplex after the elution step and when the first fluorescence label or the second fluorescence label is excited. By way of example, the emitting wavelength of the first fluorescence label may fall within the excitation wavelength of the second fluorescence, such that when the first fluorescence label is excited, the emission from the first label may excite the second signal, and that FRET may occur if the first and the second labels are within close proximity. Conversely, the emitting wavelength of the second fluorescence label may fall within the excitation wavelength of the first fluorescence label. Example of the first and second labels may include but are not limited to Alexa 488 vs Alexa 555, FITC (520 nm) vs TRITC (550 nm), and Cy3 (566 nm) vs Cy5 (649 nm). FRET only occurs when the first and the second labels are within close proximity, such as when they both exist in the same immunocomplex. This feature further enhances the specificity because only signals from liberated detection antibody that is bound to the competing molecules are quantified and used to calculate the amount of the antigen of interest in the sample.

In another embodiment, the detection of the complex between competing molecule and detection antibody in the elution buffer can be achieved through amplified luminescent proximity homogeneous assay (AlPHA assay). The detection antibody and competing molecule can be differently labeled with flurosence or luminescence signal, and the intensity signals are achieved only when the competing molecule is in close proximity to the detection antibody to eliminate non-specific signal in Zestern analysis.

DETAILED DESCRIPTION

Unless otherwise defined in this disclosure, all technical and scientific terms used herein have the same meaning as is commonly understood by one of skills in the art to which this invention belongs. All publications and patents referred to herein are incorporated by reference.

The disclosure provides methods useful for detecting and quantifying antigen or antibody in a sample. The disclosure provides a significant improvement over conventional Western blot (Burnette, W. N., 1981), Dot blot (Hawkes, R et al, 1982), and ELISA techniques (Engvall E. et al, 1971$^a$, 1971$^b$, and 1972) and allow for simple, fast, specific and quantifiable immunological analysis of the antigen of interest in a sample. The disclosed methods may also allow large scale analysis of antigen of interest in clinical, pharmaceutical and biomedical research.

Figure 1:
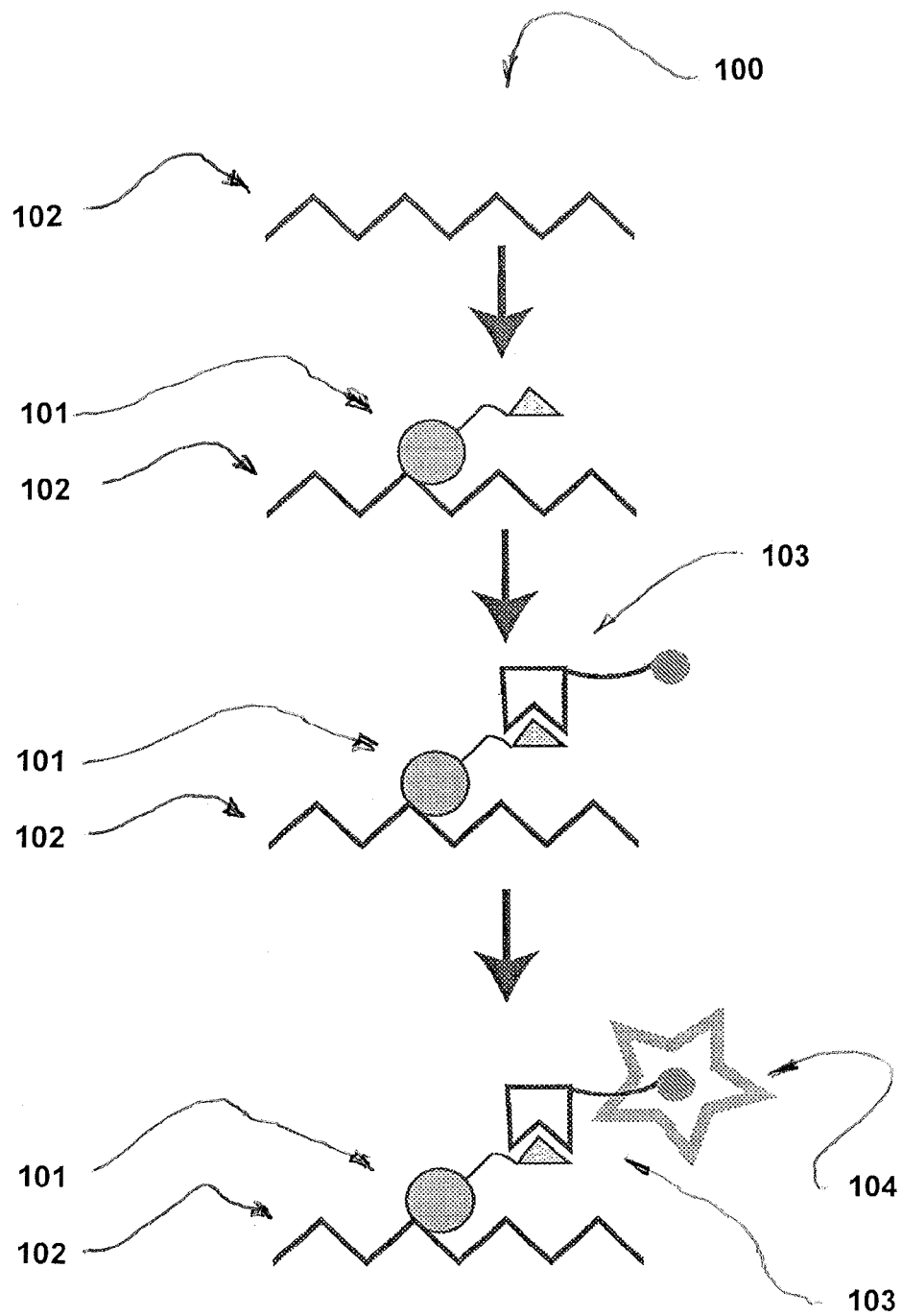
FIG. 1 shows a generalized illustration of conventional immunodetection process. 100: immunodetection process; 101: sample with antigen of interest; 102: membrane; 103: detection antibody; and 104: labeling method.

Conventional immunodetection analysis may be summarized into three parts, as demonstrated in FIG. 1. Those skilled in the art will know how to prepare samples for immunodetection analysis 100. The samples 101 may contain, among others, a chemical molecule, a peptide molecule, a protein molecule, an RNA molecule, a DNA molecule, a traditional antibody containing two heavy chains and two light chains, a recombinant antibody or fragment thereof, a bacterial cell, a virus particle, a cell, a particle, or a product comprising any two or more of the above connected by crosslinking.

Those skilled in the art will know how to apply samples 101 to membrane 102, which may include, but not limited to direct application in Dot blot analysis, gel electrophoresis and blot transfer in Western blot analysis, and coating of multi-well plates in ELISA assay.

Those skills in the art will know how to block the membrane 102, which includes, but not limited to using blocking buffer consisting of 5% non-fat milk, or 2% BSA in either PBS or TBS buffer supplemented with 0.1% Tween 20. Variations of the concentration and substitutes of these reagents are known in the art.

Those skills in the art will know how to incubate the antibody 103 with prepared samples. While conventional method include steps of incubation of primary antibody, wash and incubation of secondary antibody with membrane, there are known variations among these steps, yet, not departing from the broad inventive concept of current invention.

Those skills in the art will know how to detect the results in conventional immunodetection analysis 100. There are multiple methods to either directly label 104 the primary antibody, or indirectly labeled with the secondary antibody 104 to give readout of the amount of the bound immunocomplex on membrane in the detection process. For example, enzymatic coupling of the antibody, radiolabeling with antibody, or labeling the antibody with fluorescent dye, and the readout can be detected either through visual inspection in a color reaction, or through X-ray film when antibody is labeled with radioactive materials. While these variations are extensive, they are not departing from the broad inventive concept of current invention.

Figure 2:
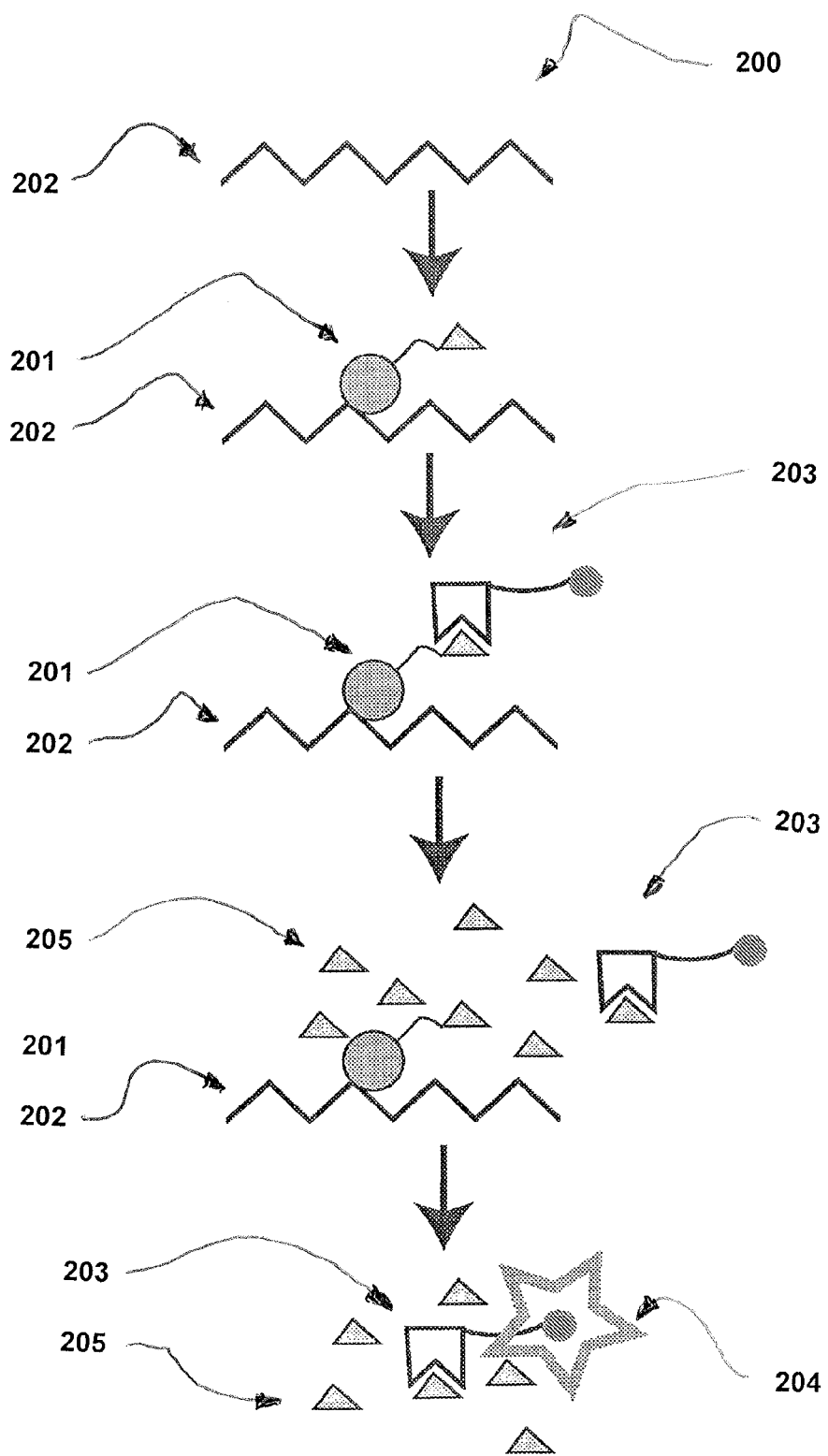
FIG. 2 shows a generalized illustration of one embodiment of Zestern, the improved immunodetection process. 201: sample with antigen of interest; 202: membrane; 203: detection antibody; 204: labeling method; 205: competing molecule.

In this invention, an additional elution step is included in the conventional immunodetection analysis, between the blocking/incubation/washing step and detection step, as demonstrated in FIG. 2. The membrane-bound antigen-antibody immunocomplex 201/203 formed in the blocking/incubation/washing step is exposed to competing molecule 205, either in single copy or in multiple copies in a single molecule, in elution buffer. The reporter enzyme-labeled antibody 203/205, freed from antigen-antibody immunocomplex 201/203, is released into elution buffer from membrane. In the detection step, reporter assay is initiated in the elution buffer rather than on the surface of the membrane, allowing for direct quantification of the readout of the reporter assay.

By including an elution step in the otherwise conventional immunodetection process, this invention improves specificity of the Dot blot analysis, allowing the result to be directly quantifiable. Moreover, this invention preserves the advantage of the Dot blot analysis of being fast and simple, allowing for its large-scale applications and in multi-unit plate format.

Furthermore, this invention provides an additional advantage over the conventional immunodetection process. In conventional immunodetection analysis, the signal readout is "on the spot," in other words, the immunocomplex being detected remains bound to the membrane through its tight association with the bound antigen of interest. A deviation of this invention from conventional immunodetection analysis is that the labeled antibody is freed from the immunocomplex bound on the membrane into the elution solution to avoid any possible physical limitation of the membrane in the detection process. For example, a common practice of immunodetection in both Dot blot and Western blot analyses is to label the antibody with horseradish peroxidase, which converts ECL substrate into chemiluminescent signals "on the spot" of the membrane. The chemiluminescent signal intensity is manifested with the help of a chemiluminescence sensitive film, and quantified indirectly through densitometric analysis. The overall process is complicate and inaccurate in nature. Current invention, on the other hand, eliminates the need of film and densitometer in this process to quantify freed antibody labeled with horseradish peroxidase directly in elution buffer using microplate luminometer. While this specific example merely serves to illustrate the advantage of current invention, it needs to be understood that the invention is not limited thereto.

Furthermore, the invention also retains the advantage of the ELISA assay while increases the binding capacity and loosens the demand on the specificity of the antibody. The inclusion of an excessive amount of the competing molecule in the elution step allows only those antibodies bound to the antigen of interest being liberated from the membrane, preventing any interference from non-specific interactions commonly observed in current biological research. Therefore, the availability of the suitable antibodies for immunodetection in multi-unit plate format increases significantly as a result of this invention.

For purpose of this disclosure, the solid phase may be a membrane, a slide, a plate, a multi-unit plate or a plurality of beads. One embodiment of multi-unit plate is multi-well plate. As used therein, "membrane" is to be taken into its broadest context. A membrane can be any material with sufficient surface porosity to allow access by detection antibodies and a suitable surface affinity to bind antigen. All these materials may be used in suitable shapes, such as films, sheets, or plates; or, they maybe coated onto or bonded or laminated to appropriate insert carriers, such as paper, glass, plastic materials or fabrics. For example, a membrane can be, but not limited to, nitrocellulose membrane, PVDF membrane, or a multi-well plate in ELISA assay.

As used herein "reporter enzyme" is to be taken in its broadest context. A reporter enzyme can be any modification of the antibody in immunodetection assay with the purpose to aid the detection of the antibody. For example, a report enzyme can be, but not limited to, antibody directly labeled with radioactive isotope like Iodide 125, or reporter enzymes like alkaline phosphatase or horseradish peroxidase. The detection of the amount of reporter enzymes associated with antibody is through the formation of a detectable product as the readout of the amount of reporter enzymes in the detection reaction. The product can be radioactive, luminescent, fluorescent, or a product with characteristic absorbance or reflection spectrum in the visible or outside the visible range. When a complement is used to detect the bound antigen-antibody complex, it may either be labeled in any one of the above ways, or be detected in turn by a specific anti-complement antibody.

As used herein "antigen" and an "antibody" are to be taken in their broadest context. An "antigen" can be a molecule, a cell, a virus, or a particle. The term "antigen" may be used to refer to a chemical compound, a peptide, a protein, an RNA, a DNA, a cell (proteins released in situ), or a virus particle (proteins released in situ) or any molecules that may evoke the production of one or more antibodies by a host animal, including human. An antigen may also be a product comprising any two or more of the molecules or moieties crosslinked together. An antigen can exists either in a pure form, or it can exist in a mixture. An antigen can be in a modified form (e.g., modified by a chemicals) or be in an unmodified form.

Reference herein to an "antibody" is to be taken in its broadest context. An "antibody" is a polypeptide that binds to "an antigen". An antibody includes, but is not limited to, a traditional antibody, a fragment of a traditional antibody containing an antigen binding site, a recombinant antibody containing an antigen binding site, a protein which binds to an antigen, and a product that comprises of crosslinking any two or more of the above. An antibody can exist either in a pure form, or in a mixture. An antibody can be in a modified form (e.g., modified by a chemical) or be an unmodified form.

Reference herein to an "elution step" is to be taken into its broadest context. "Elution" is to free an antibody labeled directly, or indirectly through a secondary antibody with a reporter enzyme, from a bound immunocomplex containing the antigen of interest on the membrane using competing molecule or any molecule sharing the same binding site or sites of the antibody with the antigen of interest. It also includes, but is not limited to, molecule that does not share the same binding site of the antibody, but can disrupt the bound immunocomplex on the membrane while maintain the specificity of the immunodetection process. The competing molecule can exist in single copy, or in multiple repeats in a single molecule for this purpose.

As used herein "competing molecule" is to be taken in its broadest context. An "competing molecule" may be used to refer to a chemical compound, a peptide, a protein, an RNA, a DNA, a cell (protein released in situ), or a virus particle (proteins released in situ) or any molecules that may disrupt the immunocomplex formed between antigen and detection antibody through competition. A competing molecule may also be a product comprising any two or more of the molecules or moieties crosslinked together. A competing molecule can exists either in a pure form, or it can exist in mixture. A competing molecule can be in a modified form (e.g, modified by a chemicals) or be in an unmodified Form. Competing molecule can be the complete molecule of the antigen, or part of the antigen of interest if this part of the molecule is known to be able to compete with the antigen of interest in the bound antigen-antibody immunocomplex. In the case where the epitope against a specific antibody is known, a competing molecule here can be the epitope peptide in single or multiple copies.

In one aspect, the invention provides an improved Dot blot analysis with modifications. The process begins with application of prepared samples containing antigen of interest to membrane, preferably in a multi-unit plate format. The non-specific protein binding site on the membrane is blocked, followed by the addition of the antibody labeled directly with reporter enzyme, or the addition of primary antibody followed by the secondary antibody labeled with reporter enzyme after successive washes. Unbound antibodies are washed away in the wash buffer without interfering with the established antigen-antibody interaction. The bound antibodies on the membrane, through antigen-antibody interaction, are eluted with solution containing competing molecule. The amount of liberated antibody labeled with reporter enzyme is measured directly in the elution solution through formation of reporter enzyme-mediated product, without the necessity of a medium, such as X-ray film.

In one aspect, the invention is to simplify the conventional Western blot analysis technique by eliminating the gel electrophoresis step to allow for large-scale analysis of protein samples in experimental, clinical and pharmaceutical settings. The results of the protein analysis can also be directly quantified, thus eliminating the inherited inaccuracy associated with the conventional methods.

Another objective of the invention is also to simplify the complicated developmental process associated with the ELISA assay. The current invention, with the inclusion of a serie of dosage of competing molecule as standard, can easily be translated into an ELISA assay with the same accuracy yet increased binding capacity and availability of suitable antibodies.

Another objective of this invention is also to increase the efficiency of conventional protein analysis techniques. The process begins with application of prepared samples containing multiple antigens of interest onto the membrane, and following a blocking step and the incubation of the membrane with a mixture of antibodies against each individual antigen of interest simultaneously. The addition of elution step in this invention allows for the liberation of individual antibody (directly or indirectly labeled with reporter enzyme) from its very bound immunocomplex using elution solution containing competing molecule for the very antibody without interfering with bound immunocomplexes of other antibodies and their respective antigen of interest. Direct quantification of the amount of reporter enzyme coupled with individual antibody in elution buffer determines the amount of antigen of interest in prepared sample. Repeated elution steps using each individual competing molecule lead to the quantification of every antigen of interest in prepared sample stepwise in a short time span.

Another objective of this invention is also to be used in protein microarray analysis. The process begins with the application of prepared samples in a multi-unit plate format. The bound multi-unit plate with test antigens of interest is blocked to eliminate any non-specific protein binding sites, followed by simultaneous incubation with multiple antibodies labeled directly or indirectly with reporter enzyme. The multi-unit plate is to be loaded with elution buffer, with each well holding a different competing molecule of test antigens of interest to be examined, and the incubation of the elution buffers liberates its matching antibody from bound immunocomplex in each unit of the multi-unitplate. The elution buffer is separated from the solid phase of the multi-unit plate, and quantified of the relative amount of different test antigen of interest in each well through reporter enzyme-mediated reaction simultaneously.

The simplicity of the process is also to be used in automatic process. Compared with conventional methods, the steps necessary for immunodetection analysis in this invention are limited to incubation and changing of different solutions, thus simplifying the overall process significantly, allowing for large-scale automatic process in clinical, experimental, and pharmaceutical research and for diagnostics purpose.

Another objective of this invention is to significantly improve its specificity through FRET (Sekar et al, 2003). or FRET-Like technologies including amplified luminescence proximity homogenous assay (ALPHA assay) (Bosse et al, PerkinElmer application note). It is unavoidable that certain percentage of detection antibodies would be washed off the solid phase alone or together as a immunocomplex independently from the presence of competing molecule in the elution buffer. This phenomenon may be loosely defined as background elution. Although background elution never becomes a major issue in a traditional immunoblot process, it may significantly compromise the specificity of the assay, especially when the antigen of interest in certain samples is extremely low. It is conceivable that with increased concentration of competing molecule in the elution buffer, this trend of background elution may be increased due to various factors.

FRET based assay and ALPHA assay occur only when two molecule are in close proximity. By labeling the detection antibody and competing polypeptide with paired fluorscence or luminescent dyes to achieve FRET effect or amplified signal in ALPHA assay, the specificity of the assay is significantly improved as only detection antibody eluted due to competition may be recorded as valid signal, while the interference from background elution would be significantly reduced in the detection process.

It would be appreciated by those skilled in the art that other technology may exist to achieve the same goal like FRET or ALPHA technologies, without departing from the broad inventive concept thereof. It is understood, therefore, that this invention is not limited to FRET or FRET-like technologies disclosed herein; rather, the FRET technology is disclosed to exemplify modifications that are within the spirit and scope of the invention.

It will be appreciated by those skilled in the art that changes could be made to the embodiments described above without departing from the broad inventive concept thereof. It is understood, therefore, that this invention is not limited to the particular embodiments disclosed, but is intended to exemplify modifications that are within the spirit and scope of the invention, as defined by the appended claims.

The following examples of the method of invention are to further illustrate of the nature of the invention. It needs to be understood that the invention is not limited thereto.

EXAMPLES

Example 1

Improved Method (Zestern) for Analysis of FLAG-Tagged IRS-2 Protein Expression in HEK-293 Cells HEK-293 cells were transfected using Fugene 6 method of 2 µg/60 mm dish of FLAG-tagged IRS-2 construct. After 48 hours of transfection, total cell lysates were prepared in lysis buffers containing protease inhibitors (Zhang, J., 2007). Total cell lysates were resuspended in 4×SDS sample buffer (Laemmli buffer), and heated for 5 minutes at 75° C. before they were applied to the individual units of PVDF membrane following standard Dot blot procedure. These individual units of PVDF membrane were blocked with blocking buffer (5% no-fat milk in Tris buffered saline supplemented with 0.1% of Tween 20 (commonly known as "TBST") for 1 hour before they were exposed to M2 FLAG antibody (Sigma, St. Louis) in blocking buffer at 1:1000 dilution for 2 hours, followed by 3×5 minutes wash of TBST buffer, and 2 hours of incubation in Donkey anti-mouse secondary antibody at 1:5000 dilution. After another 3×5 minutes of wash with TBST buffer, these individual units of PVDF membrane were incubated with 100 µl of elution solution (1×PBS containing 3×FLAG peptide (Sigma, St. Louis, Mo.) at final concentration of 150 ng/µl) for another 1 hour to elute bound antibodies (primary antibody bound with reporter enzyme-labeled secondary antibody) from individual unit of PVDF membrane). The elution solution of 50 µl was transferred to a 96 well black flat bottom plate, and mixed with 50 µl of prepared ECL solution (GE healthcare) before it was quantified in a standard luminometer.

The luminometer readings (arbitrary unit) are shown below in Table 1.

TABLE 1

Luminometer readings of antibodies eluted by specific antigens

| Sample | Luminometer readings (arbitrary unit) |
| --- | --- |
| Blank | 98 +/− 5 |
| Total cell lysates from mock transfected cells eluted with 3XFLAG peptide | 211 +/− 20 |
| FLAG-IRS-2, eluted with 3X FLAG peptide | 34023 +/− 3265 |
| Total cell lysates from cells transfected with FLAG-IRS-2 and eluted with TBS alone | 1041 +/− 130 |

The result is the average of three repeats in duplicate.

Example 3

Improving the Specificity of Zestern Analysis

HEK-293 cells is transfected with FLAG-IRS-2 plasmid as described in Example 1. Total cell lysate is applied to an individual unit of membrane. The membrane is blocked with a blocking buffer (5% Milk in TBST) for 1 hour before they are incubated with M2 primary antibody against FLAG epitope for 3 hours. The membrane is washed 3 times with TBST buffer for 5 minutes each. The membrane is then incubated with donkey-anti-mouse antibody labeled with Alexa 488 for another 2 hours. The individual membrane unit is washed again in TBST buffer for 3 times, each time being 5 minutes.

Excessive amount of 3×FLAG peptide labeled with Alexa 555 is incubated with individual unit of membrane for 30 minutes. The elute is transferred to multi-well plate, and analyzed under condition when the FRET effect may be detected. The proximity of the competing molecule and detection antibody ensures the FRET effects and the specificity of the assay.

LIST OF REFERENCES

The following references, patents and publication of patent applications are either cited in this disclosure or are of relevance to the present disclosure. All documents listed below, along with other papers, patents and publication of patent applications cited throughout this disclosures, are hereby incorporated by reference as if the full contents are reproduced herein.

1. Burnette, W. N. "Western Blotting": Electrophoretic transfer of proteins from Sodium Dodecyl sulfate-Polyacrylamide gels to unmodified nitrocellulose and radiographic detection with antibody and radioiodinated protein A. Analytical Biochemistry (1981) V. 112, pp. 195-203.
2. Hawkes, R., Niday, E., Gordon, J. A Dot-immunobinding assay for monoclonal and other antibodies. Analytical Biochemistry (1982) V. 119, pp. 142-147.
3. Engvall, E., Perlmann, P. Enzyme-linked immunosorbent assay (ELISA) Quantitative assay of immunoglobulin G. Immunochemistry (1971) V. 8, pp. 871-874.
4. Engvall, E., Jonsson, K., Perlmann, P. Enzyme-linked immunosorbent assay II. Quantitative assay of protein antigen, immunoglobulin G, by means of enzyme-labeled antigen and antibody-coated tubes. Biochemica et biophysica acta (1971) V. 251, pp. 427-434
5. Engvall, E., Perlmann, P. Enzyme-linked immunosorbent assay, ELISA III. Quantitation of specific antibodies by enzyme-labeled anti-immunoglobulin in antigen-coated tubes. The journal of Immunology (1972) V. 109, pp. 129-135.
6. Yalow, R. S., Berson, S. A. Immunoassay of endogenous plasma insulin in man. Journal of Clinical Investigation (1960) V.39, pp. 1157-1175.
7. Zhang, J. The direct involvement of SirT1 in insulin-induced insulin receptor substrate-2 tyrosine phosphorylation (2007). V. 282, pp. 34356-34364.
8. Sekar, R. B., Periasamy, A. Fluorescence resonance energy transfer (FRET) microscopy imaging of live cell protein localizations (2003). V. 160, pp. 629-633.
9. Bosse, R., Illy, C., Chelsky, D. Application note: Principles of AlphaScreen. Amplified Luminescent ProximityHomogenous assay. PerkinElmer Life Sciences. AlphaScreen application note ASC-001

What is claimed:

1. A process for measuring the amount of an antigen in a sample comprising the following steps:
   a. binding the antigen to a solid phase;
   b. forming an antigen-antibody immunocomplex on the solid phase by applying a detection antibody that is specific for the antigen;
   c. liberating the detection antibody from the immunocomplex by applying a competing molecule that disrupts the immunocomplex by competing against the antigen for binding to the detection antibody;
   d. collecting the liberated detection antibody; and
   e. quantifying the liberated detection antibody to measure the amount of the antigen in the sample.

2. The process of claim 1 in which the antigen is bound to the solid phase by applying at least part of the sample to the solid phase.

3. The process of claim 1 in which, before forming the immunocomplex, the solid phase is blocked to prevent binding of detection antibody to the solid phase that is not mediated by the antigen.

4. The process of claim 1 in which, after forming the immunocomplex but before liberating the detection antibody, any unbound detection antibody is removed from the solid phase.

5. The process of claim 1 in which the antigen is selected from the group consisting of a polypeptide, a chemical, an RNA, a DNA, a cell and a virus particle.

6. The process of claim 1 in which the competing molecule is a polypeptide.

7. The process of claim 6 in which the polypeptide comprises further antigen.

8. The process of claim 6 in which the polypeptide comprises an epitope of the antigen that is specific to the detection antibody.

9. The process of claim 6 in which the polypeptide comprises the detection-antibody-interacting region of the antigen.

10. The process of claim 6 in which the polypeptide comprises multiple copies of the detection-antibody-interacting region of the antigen.

11. The process of claim 6 in which the polypeptide comprises a polypeptide that binds more strongly to the detection antibody than does the antigen.

12. The process of claim 1 in which the detection antibody is labeled.

13. The process of claim 12 in which the method of labeling is selected from the group consisting of radio labeling, infrared labeling, fluorescence labeling and reporter-enzyme labeling.

14. The process of claim 12 in which the detection antibody is labeled through a secondary antibody.

15. The process of claim 12 in which the competing molecule is labeled differently from the detection antibody.

16. The process of claim 15 in which the labeled competing molecule pairs with the differently-labeled detection antibody to improve the specificity of the process.

17. The process of claim 16 in which the detection antibody is labeled through a secondary antibody.

18. The process of claim 16 in which the method of pairing is selected from the group consisting of a FRET-based method and an amplified luminescence proximity homogeneous assay.

19. The process of claim 1 in which the solid phase is a porous material.

20. The process of claim 19 in which the porous material is sufficiently porous to allow penetration by the detection antibody.

21. The process of claim 1 in which the solid phase is chosen from the group consisting of a membrane and a multi-unit plate.

22. The process of claim 1 in which the form of the solid phase is selected from the group consisting of a film, a sheet and a plate.

23. The process of claim 1 in which the solid phase comprises a material selected from the group consisting of paper, glass, plastic and fabric.

24. The process of claim 1 in which the solid phase is an ELISA plate.

25. The process of claim 1 conducted in an automated assay.

26. A process for measuring the amounts of multiple antigens in a sample comprising the following steps:
   a. taking sub-samples from the sample;
   b. separately processing each sub-sample by at least the following steps:
      (1) binding the antigen to a solid phase;
      (2) forming an antigen-antibody immunocomplex on the solid phase by applying a detection antibody that is specific for the antigen;
      (3) liberating the detection antibody from the immunocomplex by applying a competing molecule that disrupts the immunocomplex by competing against the antigen for binding to the detection antibody;
      (4) collecting the liberated detection antibody; and
      (5) quantifying the liberated detection antibody to measure the amount of the antigen in the sample.

27. A process for measuring the amounts of a plurality of antigens in a sample comprising the following steps:
   a. binding the plurality of antigens to a solid phase;
   b. forming a plurality of antigen-antibody immunocomplexes on the solid phase by applying a plurality of detection antibodies, each of which is specific for one of the plurality of antigens;
   c. liberating one of the detection antibodies from the solid phase by applying a competing molecule that disrupts the immunocomplex formed by said detection antibody and the corresponding antigen;
   d. collecting said liberated detection antibody;
   e. repeating steps (c) and (d) for at least one other detection antibody; and
   f. quantifying each liberated detection antibody to measure the amount of the corresponding antigen in the sample.

28. A process for measuring the amounts of antigens in a multi-antigen sample comprising the following steps:
   a. taking sub-samples from the sample;
   b. applying each sub-sample to a separate solid phase;
   c. binding the antigens in each sub-sample to the sub-sample solid phase;
   d. forming antigen-antibody immunocomplexes on each sub-sample solid phase by applying test detection antibodies that are specific for test antigens correspondingly on the solid phase;
   e. performing the following steps with a sub-sample:
      (1) applying to the sub-sample solid phase a competing molecule specific to a test antigen that disrupts immunocomplexes with the antigen by competing against the antigen for binding to the corresponding test detection antibody;
      (2) liberating the test detection antibody from the immunocomplexes formed with that test antigen;
   f performing step e(1) and e(2) with other sub-samples, in each case applying a competing molecule specific to a different test antigen;
   g. collecting the liberated test detection antibodies; and
   h. quantifying the liberated test detection antibodies to measure the amount of the test antigens in the sample.

\* \* \* \* \*